(12) United States Patent
Gerges et al.

(10) Patent No.: US 12,161,779 B2
(45) Date of Patent: Dec. 10, 2024

(54) THREE-DIMENSIONAL IMPLANTABLE MATRIX WITH REDUCED FOREIGN BODY RESPONSE

(71) Applicant: TENSIVE SRL, Milan (IT)

(72) Inventors: Irini Gerges, Milan (IT); Alessandro Tocchio, Milan (IT); Federico Martello, Milan (IT); Margherita Tamplenizza, Milan (IT); Giulia Maria Foscarina Chincarini, Milan (IT); Stefano Koman, Milan (IT)

(73) Assignee: TENSIVE SRL, Milan (IT)

( * ) Notice: Subject to any disclaimer, the term of this patent is extended or adjusted under 35 U.S.C. 154(b) by 0 days.

(21) Appl. No.: 18/030,149

(22) PCT Filed: Oct. 6, 2020

(86) PCT No.: PCT/IB2020/059352
§ 371 (c)(1),
(2) Date: Apr. 4, 2023

(87) PCT Pub. No.: WO2022/074427
PCT Pub. Date: Apr. 14, 2022

(65) Prior Publication Data
US 2023/0270918 A1     Aug. 31, 2023

(51) Int. Cl.
*A61L 27/36* (2006.01)
(52) U.S. Cl.
CPC ..... *A61L 27/3633* (2013.01); *A61L 2300/604* (2013.01); *A61L 2430/34* (2013.01)
(58) Field of Classification Search
CPC .......... A61L 27/3633; A61L 2300/604; A61L 2430/34
See application file for complete search history.

(56) References Cited

U.S. PATENT DOCUMENTS

| 6,454,811 B1 | 9/2002 | Sherwood et al. |
| 9,937,278 B2 | 4/2018 | Steinberg et al. |

(Continued)

FOREIGN PATENT DOCUMENTS

| CN | 101421391 A | 4/2009 |
| CN | 101584882 A | 11/2009 |

(Continued)

OTHER PUBLICATIONS

Machine translation of CN 102137926 A from PE2E via FIT, 2011 (Year: 2011).*

(Continued)

*Primary Examiner* — Bethany P Barham
*Assistant Examiner* — Ayaan A Alam
(74) *Attorney, Agent, or Firm* — HOWSON & HOWSON, LLP

(57) ABSTRACT

An implantable and biodegradable polymeric matrix with reduced foreign body response for the regeneration and/or reconstruction and/or creation of soft and connective tissue and/or organs is provided. The matrix has a density equal to or lower than 40 kg/m³, a plurality of local thicknesses of a solid component with an arithmetic mean equal to or lower than 95 μm, an average size of pores/void spaces equal to or lower than 15,000 μm, a surface roughness $R_a$ of the solid component with an arithmetic mean equal to or lower than 3 μm; and a contact angle θ of the solid component lower than 110°, preferably in the range 10° to 90°, and more preferably in the range 30° to 60°.

19 Claims, 5 Drawing Sheets

(56) References Cited

U.S. PATENT DOCUMENTS

| | | | |
|---|---|---|---|
| 10,449,270 | B2 | 10/2019 | Ju et al. |
| 10,743,982 | B2 | 8/2020 | Gerges et al. |
| 10,799,336 | B2 | 10/2020 | Hutmacher et al. |
| 11,219,703 | B2 | 1/2022 | Beuer et al. |
| 11,577,008 | B2 | 2/2023 | Bassett et al. |
| 2011/0129924 | A1 | 6/2011 | Ying et al. |
| 2012/0239161 | A1* | 9/2012 | Datta ............ A61L 27/58 623/23.72 |
| 2013/0123939 | A1 | 5/2013 | Nauman et al. |
| 2020/0189177 | A1 | 6/2020 | Wei et al. |

FOREIGN PATENT DOCUMENTS

| | | | | |
|---|---|---|---|---|
| CN | 101632841 | A | | 1/2010 |
| CN | 102137926 | A * | 7/2011 | ............ A61K 35/33 |
| CN | 102423272 | A | | 4/2012 |
| CN | 106243376 | A | | 12/2016 |

OTHER PUBLICATIONS

Thun, Nonsteroidal anti-inflammatory drugs as anticancer agents: Mechanistic, pharmacologic, and clinical issues, 2002, Journal of the National Cancer Institute, 94, 252-266 (Year: 2002).*

James, Polyurethanes with radiopaque properties, 2005, Biomaterials, 27, 160-166 (Year: 2005).*

International Search Report and Written Opinion of the International Searching Authority issued for International PCT Application No. PCT/IB2020/059352 on Jun. 25, 2021.

I. Gerges et al., "Exploring the Potential of Polyurethane-based Soft Foam as Cell-Free Scaffokd for Soft Tissue Regeneration", Acta Biomaterialia, vol. 73, pp. 141-153, Apr. 2018 (Abstract only).

J. Kucinska-Lipka et al., "Polyurethane Porous Scaffolds (PPS) for Soft Tissue Regenerative Medicine Applications", Polymer Bulletin, vol. 75, No. 5, pp. 1957-1979, Jul. 2017 (Abstract only).

P. Singhal et al., "Ultra Low Density and Highly Crosslinked Biocompatible Shape Memory Polyurethane Foams", Journal of Polymer Science Part B: Polymer Physics, vol. 50, No. 10, pp. 724-737, Mar. 2012 (Abstract only).

P. Singhal et al., "Ultra Low Density and Highly Crosslinked Biocompatible Shape Memory Polyurethane Foams", Journal of Polymer Science Part B: Polymer Physics, vol. 50, No. 10, pp. 724-737, Mar. 2012 (Full copy).

I. Gerges et al., "Exploring the Potential of Polyurethane-based Soft Foam as Cell-Free Scaffokd for Soft Tissue Regeneration", Acta Biomaterialia, vol. 73, pp. 141-153, Apr. 2018 (Full copy).

J. Kucinska-Lipka et al., "Polyurethane Porous Scaffolds (PPS) for Soft Tissue Regenerative Medicine Applications", Polymer Bulletin, vol. 75, No. 5, pp. 1957-1979, Jul. 2017 (Full copy).

* cited by examiner

THREE-DIMENSIONAL IMPLANTABLE MATRIX WITH REDUCED FOREIGN BODY RESPONSE

TECHNICAL FIELD

The present invention relates to medical implants, and more particularly it concerns a three-dimensional (3D) biodegradable implantable matrix (or scaffold, the two terms being used interchangeably herein) with reduced foreign body response for the regeneration and/or reconstruction and/or creation of soft and/or connective tissues and/or organs.

Preferably, but not exclusively, the matrix is intended for the reconstruction and/or creation and/or regeneration of clinically relevant volumes of said tissues and/or organs. "Clinically relevant volumes", as used herein, means volumes $\geq 20$ cm$^3$. An exemplary application in which such clinically relevant volumes are needed is breast reconstruction, e.g. after lumpectomy or mastectomy.

BACKGROUND ART

The foreign body response against implantable biomaterials employed in medicine is a critical process for wound healing and tissue repair. Such a process involves many cellular events, which can be modulated according to the characteristics of the implantable biomaterial. The cellular events involved in the inflammatory and foreign body response after implantation of the biomaterial, including protein adsorption, monocyte adhesion and formation of foreign body giant cells, are related to the chemistry of the biomaterials and to their physical and morphological characteristics (Anderson, J. M. et al. "Foreign body reaction to biomaterials", Seminars in immunology, Academic Press, 2008, pp. 86-100). The magnitude and persistence of foreign body response against the implanted biomaterial can draw the line between wound healing and implant failure. A severe foreign body response, especially in case of implantable scaffolds for tissue repair, jeopardizes not only the implant safety but also its efficacy, also in terms of integration to the surrounding/adjacent tissue and of tissue ingrowth. The drawbacks related to severe body responses can be more or less dramatic, depending on the series of local and/or systemic events involved, and can escalate from biofilm formation to fibrous capsule contracture towards tumour formation (Mempin, M. et al. "The A, B and C's of Silicone Breast Implants: Anaplastic Large Cell Lymphoma, Biofilm and Capsular Contracture" Materials, 2018, 11.12: 2393; Fitzal, F. et al. "Is breast implant-associated anaplastic large cell lymphoma a hazard of breast implant surgery?", Open Biology, 2019, 9.4: 190006.

Unlike 2D meshes and 3D scaffolds of relatively small volume (V<20 cm$^3$), large 3D scaffolds (V$\geq$20 cm$^3$) face a series of problems, which are mainly related to: (i) mechanics—the friction against the surrounding/adjacent host tissue; (ii) physics—the delayed cell colonisation and vascularisation through the inner core, due to difficulty to reach the inner core of the scaffold by cells and body fluids as the volume of the scaffold increases; and (iii) chemistry—the higher local concentration of degradation sub-products, compared to those produced from degradation of small scaffolds, which may alter e.g. the local pH of the surrounding/adjacent tissue and accordingly trigger acid-mediated inflammatory response.

A number of proposals aiming at modulating the foreign body response against implantable matrices and the regeneration of clinically relevant volumes are known.

For instance, WO 2016/038083 A1 and the related paper by Chhaya M. P. et al. "Transformation of Breast Reconstruction via Additive Biomanufacturing", Scientific Reports 2016, 6: 28030, disclose structurally stable large scaffolds for reconstruction and regeneration of clinically relevant volumes of mammary tissue obtained by 3D printing of rigid thermoplastic polymers. The average pore size of the so obtained scaffold can be easily tuned and the interconnectivity between pores can reach the maximum extent by controlling the distance between the polymeric filaments forming the solid component of the scaffold. Yet, that scaffold exhibits a mismatching between the mechanical properties of the 3D construct/matrix and those of the surrounding/adjacent tissue, due to the rigidity of the polymer combined with the relatively high local thickness (200-300 µm). This can trigger mechanically induced foreign body responses against the matrix in vivo, due to the friction against the surrounding/adjacent tissue, hindering the process of mechanically induced signalling for adipogenic differentiation of mesenchymal stem cells. For this reason, it is necessary to remedy the poor biological performance by injecting autologous lipoaspirate into the implanted scaffold, in the absence of which the nature of the tissue found inside the scaffold implanted is prevalently fibrous and poor of adipose tissue.

WO 2017/029633 A1 discloses a scaffold material to be used in manufacturing implants for soft tissue regeneration. The material is in form of a shapeable paste obtained from liquid-absorbing micro-gel particles having pores for host tissue ingrowth with an average pore size of up to some centimetres. The overall mass of dry material content of said shapeable paste is comprised between 0.1% and 10%, and thus the foreign body response against the micro-gel material is controlled by the low content of solid material in the scaffold. However, the scaffold cannot regain the original shape after deformation and accordingly cannot withstand the continuous mechanical solicitation and stress associated to patients' everyday activities. The lack of elasticity likely inhibits a correct mechanical signalling from the scaffold to the undifferentiated mesenchymal cells and also compromises the capability to supply adequate mechanical support to the newly regenerated tissue (Mitsak, A. G. et. al. "Mechanical characterization and non-linear elastic modelling of poly (glycerol sebacate) for soft tissue engineering", Journal of the mechanical behaviour of biomedical materials, 2012, 11, 3-15; Dado, D. et al. "Mechanical control of stem cell differentiation", Regenerative medicine, 2012, 7(1), 101-116). Therefore, the prior art scaffold is not particularly suitable for the regeneration of large volumes of soft tissue.

WO 2017/037649 A1 discloses a biodegradable medical device for breast reconstruction or augmentation made of soft polymeric foam. The morphological parameters of the resulting matrix are not wholly satisfactory for the purposes in view, in terms of porosity degree (80-90%, Example 1 and Table 1) and thickness of the pore walls (FIG. 2).

Ra Jo, A. et al. "Fabrication of cylindrical PCL scaffolds using a knitting technique and assessment of cell proliferation in the scaffolds", Tissue Engineering and Regenerative Medicine, 2014, 11.1: 16-22, disclose cylindrical scaffolds produced by rolling-up 2D knitted flat sheets of polycaprolactone (PCL). The characteristics of said scaffold represent a close prior art to this invention in terms of the thickness of the polymeric monofilaments (100 microns). Such a thickness is significantly lower than that of the scaffold disclosed in WO 2016/038083 A1 and in the related paper by Chhaya et al. (200-300 microns), but it is still too high for a satisfactory use in regeneration of soft/connective tissue. Indeed, the resulting high density of these scaffolds (density >200 kg/m3; porosity <78%), combined with the rigidity of PCL, makes those scaffolds more suitable for bone tissue repair (where triggering dense collagen bundles formation is a desired outcome, unlike in case of soft tissues). In fact, the biological performance of these scaffolds was assessed in vitro, using osteosarcoma cells.

Thus, there is still a need for a bioactive scaffold, capable of reducing the problems related to the excessive foreign body response against the same when implanted into a human body, especially when used in connection with clinically relevant volumes of the tissues and/or organs to be created and/or repaired.

SUMMARY OF INVENTION

The invention provides an implantable and biodegradable polymeric matrix having a solid component with interconnected pores/void spaces, characterized by:
- a density equal to or lower than 40 kg/m3, preferably in the range 5 kg/m3 to 30 kg/m3 and more preferably in the range 10 kg/m3 to 25 kg/m3;
- a plurality of local thicknesses of the solid component of the matrix with an arithmetic mean equal to or lower than 95 μm, where said plurality of local thicknesses fall in two distribution ranges, namely: (i) an upper range, preferably 20 μm to 95 μm and more preferably 25 μm to 40 μm; and (ii) a lower range, preferably 2 μm to 15 μm and more preferably 5 μm to 10 μm;

an average size of the pores/void spaces equal to or lower than 15,000 μm, preferably in the range 2,000 μm to 10,000 μm, and more preferably in the range 1,000 μm to 5,000 μm;
a surface roughness Ra of the pore walls/filaments with an arithmetic mean equal to or lower than 3 μm;
mechanical properties matching those of tissues at the implant region, which in case of soft tissue is expressed by a compression elastic modulus (Ec) in the range 0.2 kPa to 100 kPa, preferably in the range 0.2 kPa to 10 kPa and more preferably in the range 0.2 kPa to 5 kPa;
a contact angle θ of the solid component equal to or lower than 110°, preferably in the range 10° to 90° and more preferably in the range 30° to 60°.

Thanks to said characteristics, the matrix of the invention is characterized by a reduced foreign body response and a remarkably high biocompatibility.

In a first embodiment of the present invention, the matrix has a porous structure, of which the pores have heterogeneous shapes (even non-geometrical) and sizes randomly distributed throughout the matrix volume. A matrix of this kind can be produced for instance by foaming, phase separation, powder bed fusion, particulate leaching and combinations of such techniques.

In a second embodiment of the present invention, the matrix consists of a plurality of units (repeating units) of predetermined shapes and sizes with interconnected open void spaces, which units repeat along the axes of a three-dimensional structure and are formed of filaments defining the void spaces. The matrix according to said embodiment can be obtained by identically repeating "Repeating Units" of the same geometry and shape (e.g. cubic, parallelepiped, prismatic with any polygonal base or, in general, polyhedral) throughout the volume of the matrix or by combining repeating units of different shapes and geometries. A matrix of this kind can be produced for instance by weaving and/or knitting of thin fibres, sacrificial template leaching; layer-by-layer fused deposition; photolithography; stereolithography; 3D printing of thermoplastic polymers, 3D printing of photo cross-linkable precursors and combinations of such techniques.

In a preferred application, the matrix is intended for the reconstruction and/or creation and/or regeneration of clinically relevant volumes ($\geq 20$ cm$^3$) of soft and/or connective tissues and/or organs. An example of such application is breast reconstruction, and the invention also concerns a scaffold for breast reconstruction comprising the above matrix.

In a preferred embodiment, the matrix of the invention is used in several biomedical and/or pharmaceutical applications, including, without being limited to:
cell therapies;
cell delivery;
bioreactors;
decellularized matrices;
drug screening tests;
coatings for implantable devices;
in vitro and/or in vivo biological tests;
release and/or delivery of bioactive molecules, peptides, drugs;
cosmetic surgery;
implantable spacer for high precision radiation therapy and as target for radiation therapy;
as implantable device for active follow-up after tumour resection and for the early diagnosis of tumours and detection of tumour relapse;
wound healing and repair of lesioned portions of biological tissues and organs.

BRIEF DESCRIPTION OF DRAWINGS

The above and other features and advantages of the invention will become apparent from the following description of preferred embodiments made by way of non-limiting example with reference to the accompanying drawings, in which.

DESCRIPTION OF EMBODIMENTS

Figure 1:
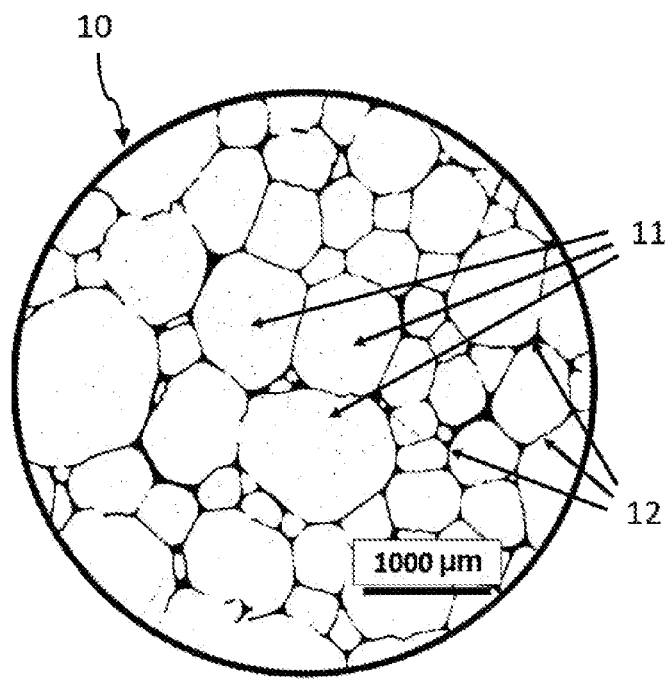
FIG. 1 shows a 2D rendering of a UCT (Ultrafast Computer Tomography) scan of a matrix according to a first embodiment of the invention.

FIG. 1 shows a matrix 10 with interconnected porous structure according to a first embodiment of the invention, obtained by foaming a polymeric precursor or a plurality of polymeric precursors during cross-linking. Pores 11 of matrix 10 have heterogeneous shapes and sizes randomly distributed throughout the matrix volume. Reference numeral 12 denotes the pore walls, which, according to the invention, exhibit a plurality of local thicknesses, as it will be discussed in more detail below.

Figure 2:
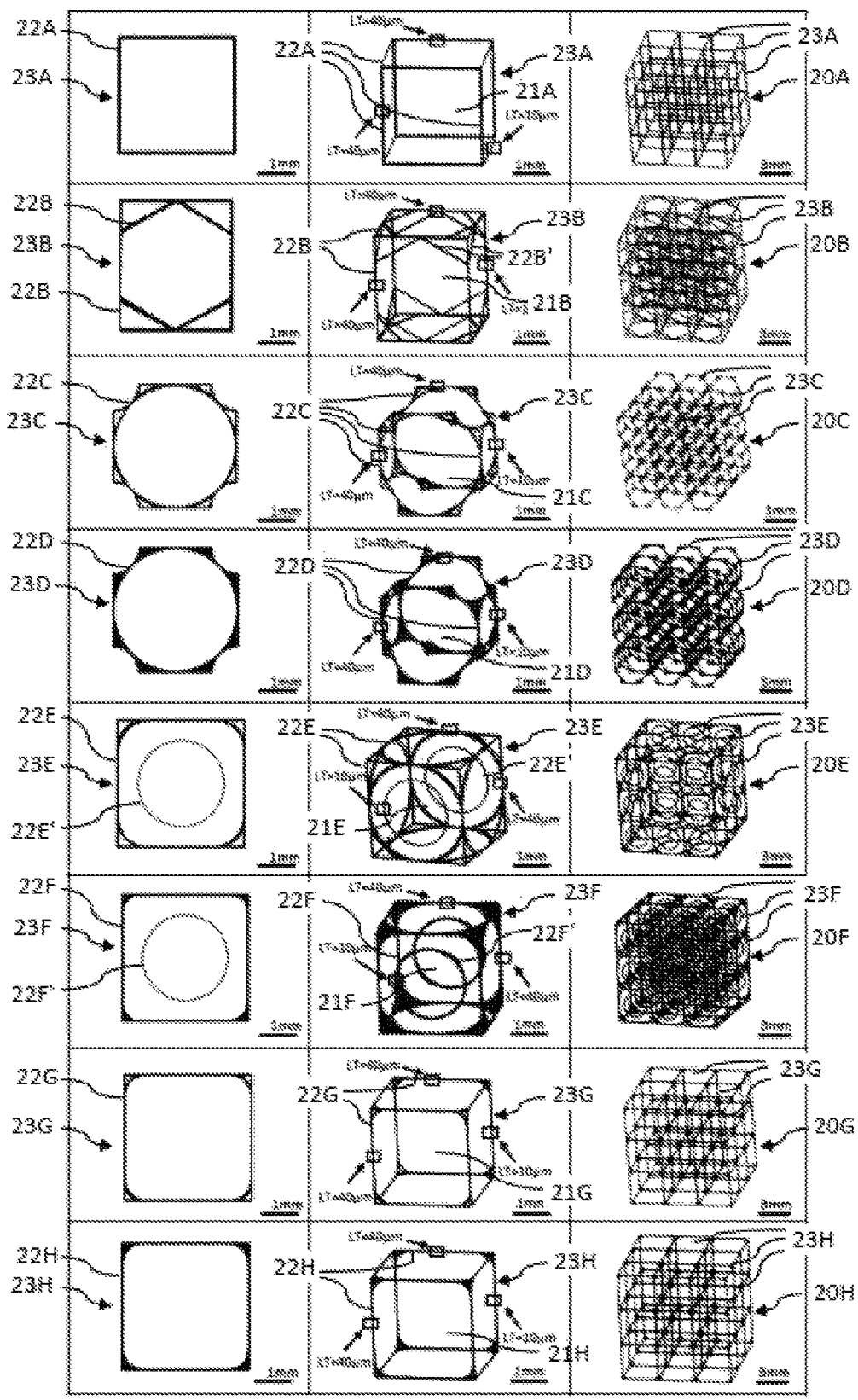
FIG. 2 is a graphical representation of the internal morphologies of a number of implantable matrices according to a second embodiment of the invention.

FIG. 2 shows the internal morphologies of some examples of implantable matrices 20A . . . 20H with interconnected network structure according to a second embodiment of the invention. Matrices 20A . . . 20H are formed by substantially cubic open templates (repeating units RUs) 23A . . . 23H of predetermined shapes, geometries and dimensions, repeating along the X, Y and Z axes and made of polymeric filaments 22A . . . 22H defining pores 21A . . . 21H. Hereinafter, suffixes A . . . H will be omitted unless specific configurations are referred to. Matrices 20 can be obtained by combining either RUs 23 of the same geometry and shape, or RUs 23 of different geometries and shapes. In the Figure, the left and middle columns are 2D and 3D representations, respectively, of exemplary RUs 23. The right column in turn shows, at each row, a portion of a matrix 20 including twenty-seven RUs 23 in a 3×3×3 array. Advantageously, the sides of the cubic RUs have an average length of a few millimetres, e.g. approximately 3 mm.

Different shapes and structures are possible for RUs 23 (cubic, parallelepiped, prismatic with any polygonal base or, in general, polyhedral), resulting in different internal morphologies of said matrix. In the examples illustrated:

RU 23A has a simple cubic shape;
RU 23B further internally contains rectilinear filaments 22W;
RUs 23C, 23D have external cubic shapes and internal cylindrical shapes, and the cube corners are substituted by concave arcs; moreover, the corner regions are hollow in RU 23C and solid (i.e. filled with polymeric material) in RU 23D;
RUs 23E, 23F, similarly to RUs 23C, 23D, have external cubic shapes and internal cylindrical shapes, and the corner regions are hollow in RU 23E and solid in RU 23F; RUs 23E, 23F further internally contain circular filaments 22E', 22F';
RUs 23G, 23H have a shape similar to RUs 23E, 23F, but lack the circular filaments.

Like pore walls 12 in FIG. 1, filaments 22 exhibit a plurality of local thicknesses. By way of example, a dual local thickness of 10 μm and 40 μm has been indicated.

Figure 3:
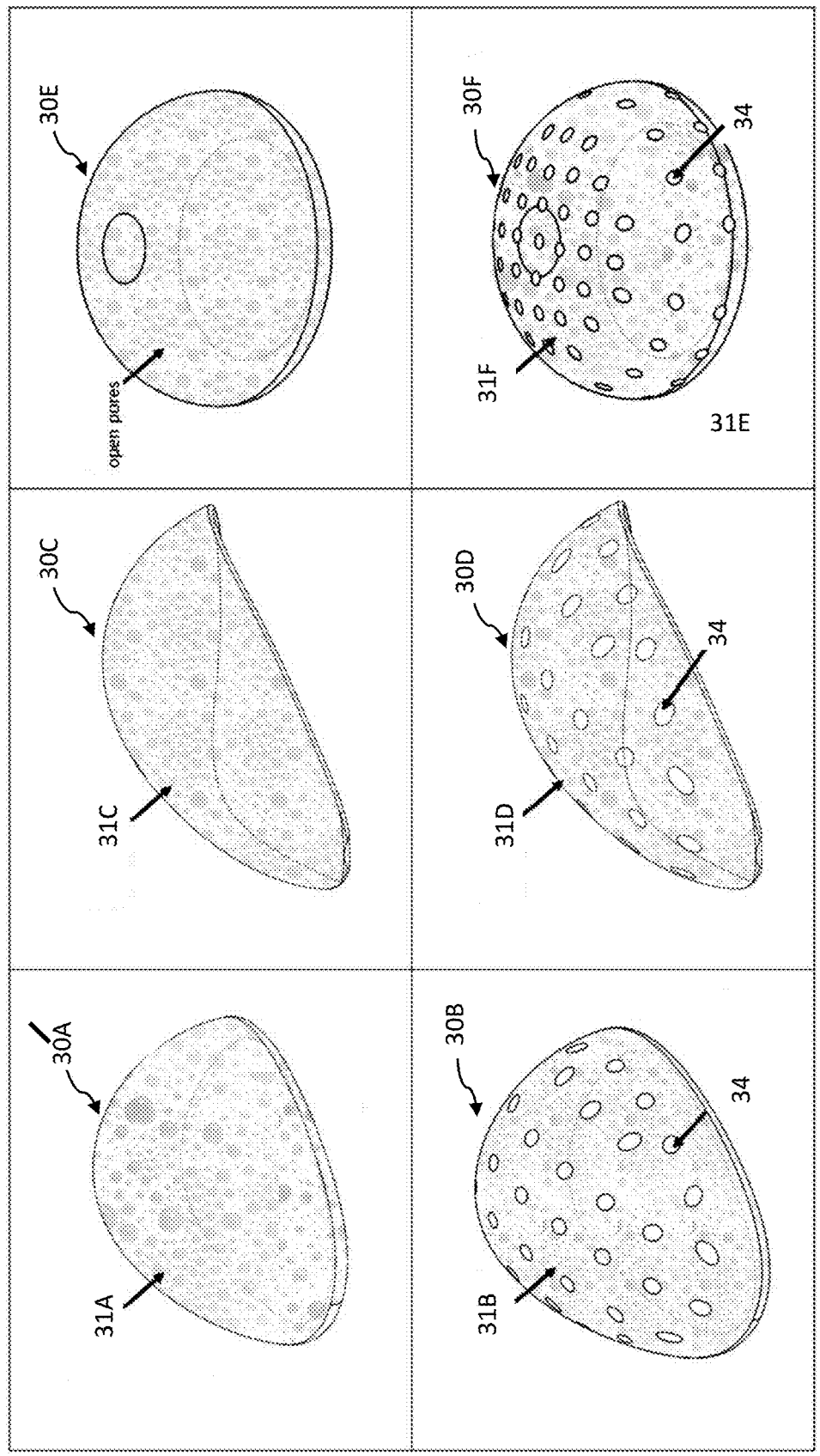
FIG. 3 is a graphical illustration of exemplary external morphologies of a number of implantable matrices according to the invention, used for the regeneration and repair of clinically relevant volumes of soft tissue.

FIG. 3 shows the external morphologies of some examples of implantable matrices 30A . . . 30F for the regeneration of large portions of soft and connective tissue (V≥20 cm³), as required e.g. in scaffolds for breast reconstruction and augmentation. Also in discussing this Figure, suffixes A . . . F for the matrices and their parts will be omitted unless specific configurations are referred to. Semi-round and flat bottomed oval matrices 30A, 30B have volume 230 cm³, length 110 mm and maximum projection 47 mm; semi-round and concave bottomed oval matrices 30C, 30D have volume 150 cm³, length 110 mm, maximum projection 47 mm; round matrices 30E, 30F have volume 220 cm³, maximum diameter 90 mm, maximum projection 45 mm, upper fillet 35 mm and lower fillet 10 mm. Whatever their geometry, matrices 30 have an internal structure with interconnected void spaces 31 (pores or open RUs as shown in FIGS. 1 and 2, respectively). As shown for matrices 30B, 30D, 30F in the bottom row of the Figure, matrices 30 can also include three-dimensional channels 34 that can be interconnected or not with the pores/void spaces or the RUs, depending on the production technique. The characteristics, the arrangement and the functions of channels 34 are disclosed in WO 2017/037649 A1. In the examples shown, the diameter of channels 34 is of the order of 5 mm and their mutual distance is in the range 5 mm to 30 mm.

Matrices 30 can be produced by any manufacturing technique allowing attaining a reduced foreign body response when implanted into a human body and the features of said matrices providing such a result, in particular in case of use for the regeneration/restoration/creation of large portions of soft and/or connective tissue, as it can occur for instance in scaffolds for breast reconstruction and augmentation. The features providing such a result will be disclosed in more detail below. Among such techniques, besides foaming already mentioned, we can cite: layer-by-layer fused deposition; phase separation; powder bed fusion; electrospinning; weaving and/or knitting of thin fibres; photolithography; stereolithography; 3D printing; particulate leaching; sacrificial template leaching. Combinations of different techniques are also possible.

More particularly, foaming, phase separation, powder bed fusion and particulate leaching are suitable for the production of a matrix where the pores/void spaces do not have a definite geometrical shape and have a random size distribution, like matrix 10 shown in FIG. 1. Weaving and/or knitting of thin fibres, sacrificial template leaching, layer-by layer fused deposition, photolithography, stereolithography, 3D printing of thermoplastic polymers or photo cross-linkable/photo-curable precursors are on the contrary suitable for the production of matrices where the pores/void spaces are of defined and similar geometry (repeating units), like matrices 20A . . . 20H shown in FIG. 2.

Examples of biomaterials that can be used for producing matrices 10, 20, 30 are synthetic polymers, natural polymers, chemically modified natural polymers, protein-functionalized natural and synthetic polymers, biomolecules and/or biomacromolecules, polynucleotides such as DNA and RNA, polysaccharides or a mixture thereof. Preferably, the polymeric material is a polyurethane-based material.

Whatever the manufacturing technique and the starting material, a matrix according to the invention, capable of reducing the problems related to the foreign body response against the same when implanted into a human body, in particular for creating and/or restoring and/or regenerating large portions (≥20 cm³) of soft and/or connective tissue, have the following features:

a density equal to or lower than 40 kg/m3, preferably in the range 5 kg/m3 to 30 kg/m3 and more preferably in the range 10 kg/m3 to 25 kg/m3;
a plurality of local thicknesses of the pore walls/filaments, with an arithmetic mean equal to or lower than 95 μm. More particularly, two distribution ranges for the local thicknesses can be identified, namely: (i) a upper local thickness range, preferably 20 μm to 95 μm and more preferably 25 μm to 40 μm; and (ii) a lower local thickness range, preferably 2 μm to 15 μm and more preferably 5 μm to 10 μm;
an average pore/void size equal to or lower than 15,000 μm, preferably in the range 2,000 μm to 15,000 μm, and more preferably in the range of 1,000 μm to 5,000 μm. Moreover, pores/void spaces with sizes in the range 2,000 μm to 10,000 μm amount to 30% to 100%, preferably 40% to 80% and more preferably 50% to 70%, of the total pore/void space count;

a surface roughness Ra of the solid component of the matrix (pore walls 12/filaments 22/material of the solid corners of RUs 23) has with an arithmetic mean equal to or lower than 3 µm;

mechanical properties matching those of the target tissue to be regenerated and/or restored and/or created. This matching, in case of soft tissue, is expressed by a compression elastic modulus (Ec) in the range 0.2 kPa to 100 kPa, preferably in the range 0.2 kPa to 10 kPa and more preferably in the range 0.2 kPa to 5 kPa.

a contact angle θ of the solid component equal to or lower than 110°, preferably in the range 10° to 90° and more preferably in the range 30° to 60°. A contact angle with such values confers enhanced hydrophilicity to the matrix.

In a preferred embodiment, different degrees of stiffness/elasticity are achieved to promote cells migration as a function of the substrate stiffness. More particularly, soft matrices may have a compression set, measured according to standard ASTM D39516, lower than or equal to 10% and an Ec. <5 kPa, whereby they have the capability to recover their original shape after a deformation up to 70% of compressive strain and 130% of tensile strain. A matrix of this kind can be easily injectable into an organism by means of a tube or a needle, hence with a minimally invasive surgical approach.

The density of the matrices according to the present invention can be measured by dividing the nominal weight (kg) of the dry matrix by the volume (m3) occupied by the matrix, including the volume occupied by the pores/void spaces, according to ASTM D3574-08 (test A, section 9-15) guidelines.

The arithmetic mean of the pore/void space sizes and the distribution thereof as a function of pore/void space count, as well as the arithmetic mean of the local thicknesses (and possibly the distribution thereof as a function of the pore wall count), can be quantified by means of UCT (Ultrafast Computer Tomography).

The surface roughness can be measured by means of atomic force microscopy (AFM), according to ISO 13565-3 guidelines.

Contact angle θ, and hence the hydrophilic character, can be determined by using the sessile drop method.

In a preferred embodiment, the void spaces/pores/RUs of a matrix are filled and temporary sealed by a bioresorbable or bioeliminable or removable material (e.g. different from the starting biodegradable material). After implantation, said material undergoes phase transition from solid to liquid state in response to chemical or physical stimuli, such as change in: the ionic force, the local temperature, pH or in response to external stimuli such as magnetic field or radiation (gamma-rays, beta-rays, X-rays), or by degradation, as result, for example, of enzymatic or hydrolytic reactions or by mechanical removal (e.g. suction). After programmed dissolution, disintegration or removal of said material, the concerned region of the matrix becomes accessible to cells and body fluids. This favours a stage-wise programmed cellular colonization in the different matrix regions.

In preferred embodiments, the matrix is:
1) coated with an integrin binding protein, polypeptide, pseudo-peptide or synthetic macromolecule(s), with the aim of enhancing the biological performance in vitro and/or in vivo, in terms of cell adhesion and biocompatibility. Non-limiting examples of integrin binders and cell adhesion molecules and macromolecules that can be immobilized on the matrix surface include: proteins, peptides, protein-peptide conjugates, polypeptides and their chemically modified derivatives, such as: collagen; gelatine; laminin; fibronectin; vitronectin; serum proteins, RGD (arginine-glycine-aspartic acid) tripeptide motif, RGD-protein conjugates, RGD derivatives, synthetic polymers containing RGD peptide-mimetic motifs in the repeating units; synthetic cell adhesive polymers such as poly(L-lysine);
2) loaded with biologically active molecules and/or drugs with the aim of regulating cell response against said matrix after implantation, to drive the process of cell differentiation and to carry out specific pharmaceutical treatments in situ;
3) filled with radio-opaque substance(s) and/or object(s) for diagnosis of tumours and diseases and for tumour relapse detection. Said radio-opaque substances and/or objects can be also immobilised on the matrix surface;
4) filled with organic and/or inorganic materials, such as metallic particles or ceramics;
5) filled with chemical probe(s) for molecular imaging diagnostics. Said probes can also be immobilised onto the matrix surface.

In preferred embodiments, the matrix optionally includes one or more of the following additional constituents:
cell-adhesion receptor activator(s), which is (are) immobilised on the matrix surface and/or is (are) inserted as a monomer or as a repeating unit into the polymeric structure of the matrix;

inhibitor(s) of collagen cross-linking enzymes, such as inhibitor(s) of lysyl-oxidase (LOX) or transglutaminase 2;

inhibitor(s) of TGF (Transforming Growth Factor)-beta cytokines activity. Said inhibitor(s) can be immobilised onto the matrix surface and/or co-polymerized to the matrix polymeric structure and/or released from the matrix to the tissue and the cells within and surrounding/adjacent to the matrix, in vitro and/or in vivo;

antitumor drugs, such as anthracyclines and taxanes.

In a preferred embodiment, the matrix can be used to release and/or deliver to the cultured cells and tissues, in vitro, and/or deliver to a local tissue near the implantation site and/or systemically via parenteral administration, in vivo, one or more of the following substances:

PPAR (Peroxisome Proliferator-Activated Receptor)-gamma activator(s); the molecules can be loaded into the matrix during its production and/or they can result from chemical or enzymatic breakdown of the macromolecular structure of the matrix itself. Non-limiting examples of PPAR-gamma activators are: (i) metabolic fatty acids, such as: linoleic acid, arachidonic acid, oleic acid, palmitic acid; lauric acid; (ii) thiazolidinediones (TZD), such as: rosiglitazone, pioglitazone and troglitazone; (iii) synthetic PPAR-gamma agonists acting also as anti-inflammatory drugs, such as: indomethacin; fenoprofen; ibuprofen; flufenamic acid.

bioactive molecules and macromolecules, antibodies, peptides, proteins, cellular components, viruses, also inactivated, or part of viruses, etc., e.g. for personalised therapeutics and preventive treatments. Said bioactive substances are initially loaded into the matrix during its production or immobilized on the matrix surface in its original state or encapsulated into micro- and/or nanoparticles;

living organisms, such as different types of cells (adult, induced pluripotent (iPS), embryonic and cord blood stem cells, differentiated cells, immune system cells, etc.), either as single cells or organized e.g. in islets or organoids and/or contained in macro- and/or microparticles.

Features mentioned above act synergistically to reduce the foreign body response against said matrix after implantation and enable correct mechanical and biochemical signalling to the newly regenerated tissue through said matrix, thereby boosting the biological performance in vivo.

In particular, the matrix confers an immediate matching softness or stiffness, comparable with that of the natural tissue surrounding/adjacent to said matrix or adjacent thereto in the implantation site or comparable to that of the target tissue to be regenerated and/or restored and/or created through said matrix.

The remarkably low local thickness, combined with the large pore/void/RU size, the surface smoothness and the enhanced hydrophilic character jointly help in challenging monocyte and lymphocyte adhesion during the very first hours after implantation and in hindering adsorption of non-specific proteins, including chemoattractant cytokines.

The multiple local thicknesses and the resulting slight difference in the pore wall/filament stiffness aim at creating a mechanical gradient on a micrometric scale. Thus, host cells can perceive mechanical cues for cell migration (mechanotaxis) through the scaffold.

The mechanical properties matching those of the target tissue, combined with the low density of the matrix, help in reducing the local friction against the surrounding/adjacent tissue and accordingly reduce the mechanical cues related to macrophage recognition of said matrix as a foreign material.

The large pore size stated above, combined with the local release of PPAR-gamma agonist and possibly of collagen cross-linking enzyme inhibitors, challenges the assembly and thickening of collagen bundles and helps hindering the stratification of fibroblasts around the scaffold, thus slowing down internal fibrosis and facilitating tissue remodelling from a fibro-vascular to a soft differentiated tissue, e.g. adipose tissue.

Moreover, the micrometric scale local thickness, combined with the matched mechanical properties and with the local release of inhibitors of collagen cross-linking enzymes, aims at reducing and/or avoiding calcification of the vascular tissue recruited through the newly regenerated tissue (Jover et al. "Inhibition of enzymes involved in collagen cross-linking reduces vascular smooth muscle cell calcification", The Faseb Journal, 2018).

The matrix according to the invention is particularly suitable for use as a scaffold for breast reconstruction after tumour resection or deformities due to trauma.

Depending on the constituents, other biomedical and pharmaceutical applications are envisaged, including, without being limited to:
- cell therapy (type I): the matrix is seeded in vitro with cells and a living tissue is harvested and cultured in vitro through said matrix prior to implantation in the host organism;
- cell therapy (type II): the matrix is implanted without cells (cell-free) and a living tissue and/or cell is treated for in vivo injection in said already implanted matrix in the host organism immediately or at a later time;
- as a bioreactor: the matrix is implanted without cells (cell-free) and left to be colonised and vascularised by the host cells before injecting the therapeutic cells into the colonised matrix;
- as a decellularized matrix: the matrix is seeded in vitro with cells and a living tissue is harvested and cultured in vitro under static and/or dynamic condition to allow production of extracellular matrix within the matrix pores. The construct matrix plus cells plus extracellular matrix is then treated according to well defined procedures to eliminate the undesired cellular component;
- in drug screening tests, wherein cells are seeded in vitro into said matrix, then the construct matrix plus cells is used to test the cellular response to the tested drug in vitro;
- as a coating for implantable devices: the matrix is placed in the interface between said device and the surrounding/adjacent tissue to reduce the foreign body reaction against the device and to minimize the capsular contracture;
- for in vitro biological tests, aiming at addressing the effects of different stimuli, including electrical and/or electromagnetic stimulations, mechanical stimulation, molecular stimulation;
- for release of bioactive molecules, peptides, drugs;
- for aesthetic and/or cosmetic procedures, such as breast augmentation and/or congenital deformities treatment;
- in wound healing and repair of lesioned portions of biological tissues and organs.

Such applications are not mutually exclusive, but can be combined together.

Non limiting examples of matrices 10, 20, 30 according to the invention are reported in the following Examples, together with suitable fabrication methods and starting biomaterials for manufacturing the same matrices.

EXAMPLES

Examples 1 to 6

The examples illustrate the preparation of low-density, flexible and soft (D≤30 kg/m3, Ec≤10 kPa) polyurethane-based biodegradable implantable matrices 10 (FIG. 1) by means of the foaming method.

Figure 4:
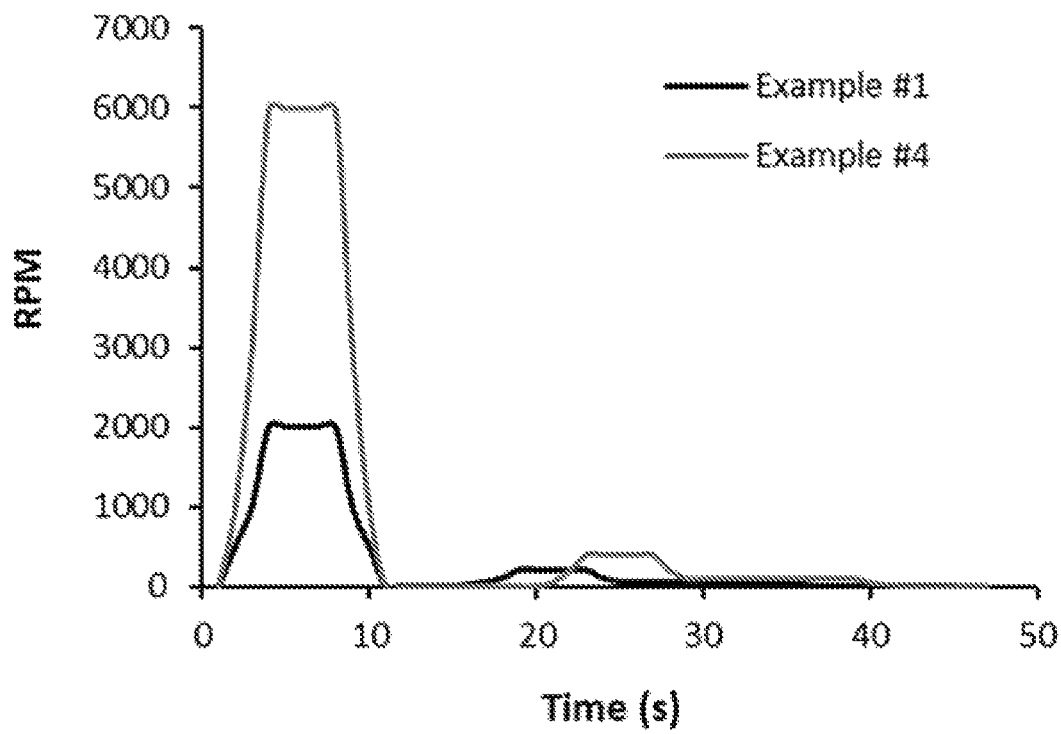
FIG. 4 is a graphical representation of two exemplary mixing profiles for producing foamed cross-linked polyurethane-based matrices according to the first embodiment of the invention.

A polyfunctional polyisocyanate-terminated prepolymer, having an average number of reactive groups per macromolecule ≥3, was crosslinked in the presence of a low molecular weight polyol, according to NCO index in the range 95 to 110, of two surface active molecules having a HLB number (difference in the Hydrophilic-Lipophilic Balance) of 4 and 12, respectively, and of an organotin-based catalyst. The reactive mixture was mixed by means of a customized metering and mixing machine, where the temperature of the reactive mixture at the mixing head was 30° C. The reactive mixture was mechanically mixed as reported in Table 1 and graphically illustrated in FIG. 4 for Examples 1 (black line) and 4 (grey line), in order to achieve a plurality of local thicknesses of pore walls 12 (FIG. 1) (mean local thickness <50 μm) and heterogeneous pore sizes (average pore size <15,000 μm), randomly distributed along the matrix volume. The mechanical mixing process included the following steps: mixing the reactive mixture for 2 to 20 seconds at 1,000 to 10,000 rpm to achieve a rapid and efficacious mixing of all components of the reactive mixture and to allow nucleation with fine air bubbles (10 μm≤Φbubble<5 μm);

- stopping the mixing for 1 to 20 seconds to preserve the stability of the micrometric air bubble nucleation;
- restarting mixing for 2 to 50 seconds at 30 to 300 rpm to homogenize the reactive mixture after collapse of a percentage of gas bubbles and to nucleate the macroscopic air bubbles (500 μm<Φbubble<10,000 μm);
- slowing down the mixing speed to 20 to 100 rpm to allow expansion of the so obtained air bubbles while preserving the raising reactive mixture from collapse or boiling, until reaching the gel point.

The cross-linked raw matrix is optionally subjected to multiple freezing-drying cycles according to the following steps:
1) performing multiple compression-decompression cycles to 80% strain at room temperature while the matrix is fully immersed in water;
2) freezing at T<−5° C. for at least 2 hours;
3) thawing;
4) draining from the unswollen water;
5) re-freezing at T<−5° C. for at least 2 hours-;
6) freeze-drying;
7) repeating steps 2) to 6) at least twice.

The morphological characteristics of the so-obtained matrices are reported in Table 2.

TABLE 1

Mechanical mixing parameters

| Example number | #1 | #2 | #3 | #4 | #5 | #6 |
|---|---|---|---|---|---|---|
| Reactive mixture volume before expansion (mL) | | | 150 | | | |
| Flow rate in the metring machine (mL/s) | 30 | 25 | 21.5 | 30 | 25 | 21.5 |
| 1$^{st}$ mixing step: speed (rpm); mixing time (s) | 2,000; 5 | 2,000; 6 | 2,000; 7 | 6,000; 5 | 6,000; 6 | 6,000; 7 |
| Stop period (s) | | 5 | | | 10 | |
| 2$^{nd}$ mixing step: speed (rpm); mixing time (s) | | 200; 5 | | | 300; 5 | |
| 3$^{rd}$ mixing step: speed (rpm); mixing time (s) | | 50; 10 | | | 100; 10 | |

TABLE 2

Morphological characteristics

| Example number | #1 | #2 | #3 | #4 | #5 | #6 |
|---|---|---|---|---|---|---|
| Average pore size (μm) | 4,000 | 3,500 | 2,000 | 1,000 | 500 | 300 |
| Local thickness (μm) | 15; 44 | 12; 40 | 10; 40 | 10; 40 | 10; 35 | 8; 30 |
| Compression elastic modulus (Ec) | 1.8 | 2 | 2.5 | 3 | 3.2 | 3.5 |
| Porosity (%) | 97.8 | 97.8 | 97.5 | 97.2 | 97.0 | 97.0 |

In order to evidence the advantages of the present invention over the prior art, a low-density matrix produced according to Example 4 (Matrix I) was compared to a high-density one produced according to Example 1 of WO 2017/037649 A1 (Matrix II). The comparison concerned both the internal morphology and the biological performance in terms of fibrous capsule formation after subcutaneous implantation in swine model. Both matrices belonged to the family of cross-linked polyurethane-ester-ether based foams.

Figure 5:
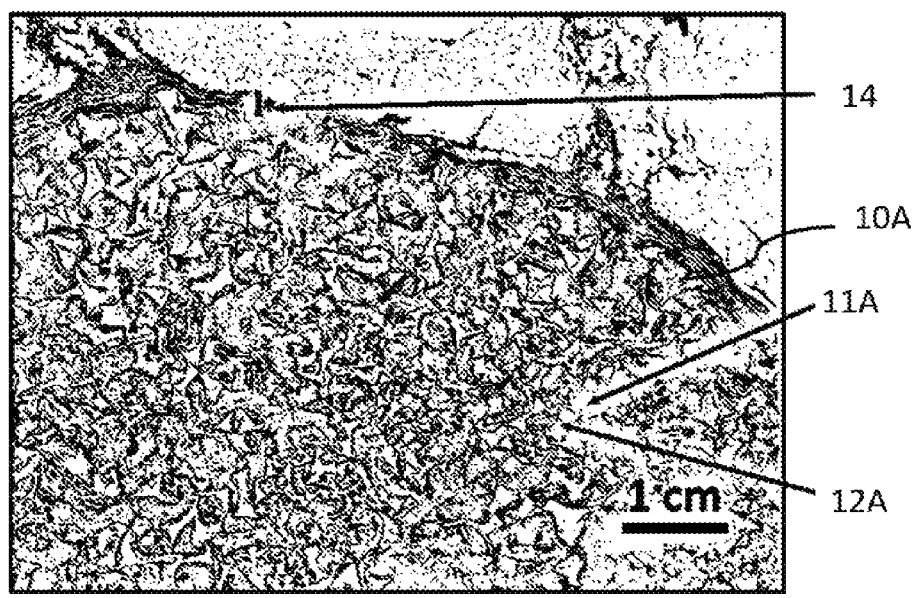
FIG. 5 is a histological image of a section of an explanted matrix (from swine animal model, after three months from implantation) according to the first embodiment of the invention, produced according to the method described in Example 1.

FIG. 5 shows a histological image of a haematoxylin and eosin (HE) stained section of an explanted Matrix I, after 3 months of subcutaneous implantation in a swine model. Elements corresponding to those shown in FIG. 1 are denoted by corresponding reference numerals, with suffix A. Reference numeral 14 denotes the external fibrous capsule, indicated also by an asterisk.

Figure 6:
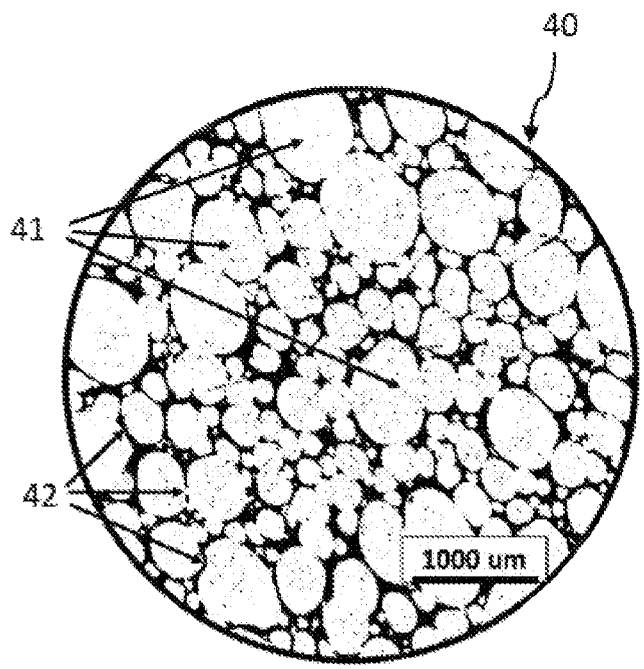
FIGS. 6 and 7 are representations corresponding to FIGS. 1 and 5, respectively, relevant to a prior art matrix.
Figure 7:
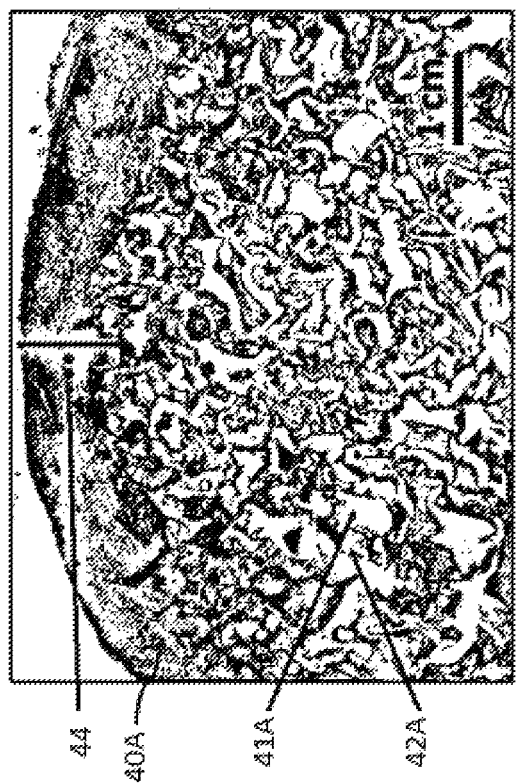

FIGS. 6 and 7 show images of the prior art Matrix II, similar to the images shown in FIGS. 1 and 5, respectively. In FIGS. 6 and 7, elements corresponding to those shown in FIGS. 1 and 5 are denoted by corresponding reference numerals, beginning with digit 4. External fibrous capsule 44 is indicated by a double asterisk.

In order to determine the morphological properties, a UCT scan was carried out for a sample from each matrix. The samples were measured with a commercially available cabinet cone-beam μCT (μCT 50, SCANCO Medical AG, Brüttisellen, Switzerland) originating from a 4 μm focal-spot X-ray tube. The photons are detected by a CCD-based area detector and the projection data are computer-reconstructed into a 3042×3042 image matrix. The scan image was segmented with a threshold for polymeric material with x-ray absorption >0.2 cm$^{-1}$ (equivalent to −120 mg HA/ccm). Image processing was carried out using IPL (SCANCO Medical AG).

The use according to the invention of two surface active molecules with HLB numbers differing by at least five points guarantees the efficacious micellization of reactive components of different hydrophilic characters and reduces coalition of pores surrounded by very thin substrate of polymeric matrix especially during the early phase of cross-linking. The mechanical mixing described above allows efficacious nucleation of the reactive mixture and fine control of the pore dimension, without need to manipulate the viscosity of the mixture by employing organic solvents, as in WO 2017/037649 A1.

The differences in terms of density, average pore size and local thickness between the two analysed samples are reported in Table 3 and are also clearly apparent at a comparison between FIGS. 1 and 6.

TABLE 3

Morphological characteristics of two polyurethane-ester-ether foam matrices, calculated by means of UCT scan.

| Morphological characteristics | Matrix I (invention) | Matrix II (prior art) |
|---|---|---|
| Density (kg/m$^3$) | 28 | 110 |
| Average pore size (μm) | 1000 | 500 |
| Arithmetic mean of the local thicknesses (μm) | 10 μm and 40 μm (two narrow local thickness distributions) | 50 μm (broad local thickness distribution, in the range 10 μm to 110 μm) |

As to the biological performance, large-volume matrices (V=25 cm$^3$) were implanted subcutaneously in female minipigs of average body weight of 50 to 70 kg for 3 months, as cell-free matrices. After sacrifice, scaffolds together with the surrounding tissues were excised and fixed in 10% neutral buffered formalin. Formalin-fixed samples were embedded in paraffin wax, sectioned at 4 μm thickness, routinely stained with haematoxylin and eosin (HE), and evaluated under a light microscope for the histological assessment of host reaction. The histological images of the stained explants in FIGS. 5 and 7 show significant differences between the thicknesses of fibrous capsules 14, 44 formed around the two scaffolds. In particular, the explanted low-density Matrix I produced according to the method described in Example 4 of the present invention was surrounded by a thin and discontinuous fibrous capsule 14 (thickness ~100 μm), whereas the high-density Matrix II produced according to Example 1 of WO 2017/037649 A1 was surrounded by a thick and compact fibrous capsule 44 (thickness ~1200 μm). Tissue ingrowth within the scaffold was shown to be partial in Matrix II due to the formation of the thick and compact fibrous capsule, while Matrix I was fully colonized by vascularized connective soft tissue.

Examples 7 and 8

Examples 7 and 8 illustrate the preparation of biodegradable implantable matrices 20 (FIG. 2) for the regeneration of clinically relevant volumes of soft tissue and organs by means of stereolithographic (SLA) 3D printing of photocurable precursors.

In Example 7, the photocurable precursor was a chemically modified chitosan photo-curable precursor having average molecular deacetylation degree in the range 30-90%. Initially, two solutions were prepared: solution A: chitosan and norbornene-carbamide NB-CA were dissolved in phosphate buffer saline solution PBS 1×pH 7.4, using an equimolar ration between NH functional groups of chitosan and NB-CA and a final concentration in solution of 20% (w/v). The functionalization of chitosan proceeded at a temperature of 40° C. to 60° C. for 5 to 35 h, away from direct exposure to light;

solution B: dipeptide cysteinyl-cysteine (thiol cross-linker) and laminin peptide (integrin binder) were mixed at a weight ratio of 1:1 in PBS 1×pH 7.4 and mechanically stirred at 200 rpm at room temperature for 20 minutes. The final concentration of solution B was 100 mg/ml.

Solution B was added dropwise to solution A under mechanical stirring at 500 rpm, until a homogenous solution was obtained, then riboflavin (photo initiator), β-aminopropionitrile (LOX inhibitor) and berberine (PPAR-gamma agonist) were added and dissolved in said mixture before loading into the chamber of the SLA-3D printing apparatus.

A CAD vector scheme of the final object was prepared and fed to the SLA-3D printing apparatus. UV-Vis light exposure was set in the visible wavelength, at 400 nm, and power was set at 5 to 15 mW/cm 2. Crosslinking is obtained in a time of 20 s to 30 s, depending on the matrix volume and the light power.

In Example 8 the photocurable precursor was a chemically modified gelatin. As in Example 7, two solutions were prepared:

solution A: gelatin type A from porcine skin having gel strength of 300 g Bloom was dissolved in PBS 1×pH 7.4 at 50° C. at the concentration of 3% (w/v). The viscosity of the gelatin solution was increased by means of coupling with norbornen-5-carboxylic acid (NO-5-CA) at the molar ratio of 1:1 between NH2 from gelatin and COOH from NO-5-CA, respectively, in presence of 1-ethyl-3-(3-dimethylaminopropyl)¬carbodiimide/N-hydroxysuccinimide EDC/NHS.

solution B: dipeptide cysteinyl-cysteine (thiol cross-linker) was mixed at a weight ratio of 1:1 in PBS 1×pH 7.4 and mechanically stirred at 200 rpm at room temperature for 20 minutes, at 50° C.

Solution B was added dropwise to solution A under mechanical stirring at 500 rpm, until a homogenous solution was obtained, then camphorquinone (photo initiator), (2-chloropyridin-4-yl)methanamine (LOX inhibitor) and berberine (PPAR-gamma agonist) were added and dissolved in said mixture before loading into the SLA-3D printing apparatus chamber.

Since the macromolecular structure of gelatin abundantly contains RGD motif, as described in Berardi, A. C. (Ed.), "Extracellular Matrix for Tissue Engineering and Biomaterials", Humana Press (2018), no additional integrin binder was added to this formulation, A CAD vector scheme of the final object was prepared and fed to the SLA-3D printing apparatus. UV-Vis light exposure was set in the visible wavelength, at 400 nm, and power was set at 10 to 20 mW/cm 2. Crosslinking was obtained in a time of 30 s to 120 s, depending on the matrix volume and the light power.

The morphological characteristics of matrices prepared according to Examples 7 and 8 are reported in Table 4.

TABLE 4

| Morphological characteristics of two 3D-printed matrices [Table 3] D-printed matrices | | |
|---|---|---|
| Examples | #7 | #8 |
| Density (kg/m$^3$) | 10-30 | 10-40 |
| Pore size (mm) | 1-3 | 1-3 |
| Average porosity (%) | 97-99 | 96-99 |
| Local thicknesses (arithmetic mean, μm) | 10; 40 | 10; 40 |
| Compression elastic modulus Ec (kPa) | 5-20 | 2-15 |

The local thicknesses of the polymeric filaments of said matrices (arithmetic mean 10 μm and 40 μm) were chosen so as to reduce the foreign body response against said matrices and to promote cell mechanotaxis during the phase of cell infiltration into and colonization of the scaffold after implantation.

It is clear that the above description has been given only by way of non-limiting example and that changes and modifications are possible without departing from the scope of the invention as claimed in the following claims.

The invention claimed is:

1. A three-dimensional biodegradable implantable matrix with reduced foreign body response for reconstruction and/or regeneration and/or creation of soft and/or connective tissue and/or organs, the matrix having a solid component with interconnected pores/void spaces exhibiting a plurality of local thicknesses with an arithmetic mean equal to or lower than 95 μm and a contact angle θ equal to or lower than 110°, the matrix being characterized by:

a density equal to or lower than 40 kg/m$^3$;

said local thicknesses of the solid component falling in two distribution ranges, namely an upper local thickness range and a lower local thickness range, wherein the lower local thickness range is 2 μm to 15 μm;

an average size of the pores/void spaces in the range 1,000 to 15,000 µm;

a surface roughness Ra of the solid component with an arithmetic mean equal to or lower than 3 µm.

2. The matrix according to claim 1, wherein
said density is in the range 5 kg/m³ to 30 kg/m³;
said upper local thickness range is 20 µm to 45 µm;
said average size of the pores/void spaces is in the range 2,000 µm to 15,000 µm, and has such a distribution that pores/void spaces with average size in the range 2,000 µm to 10,000 µm amount to 30% to 100% of the total pore/void space count;
said contact angle $\theta$ is in the range 10° to 90°.

3. The matrix according to claim 1, allowing an immediate matching between the mechanical properties of the volume filled with the matrix and the mechanical properties of the target tissue.

4. The matrix according to claim 1, wherein said tissue to be reconstructed and/or regenerated and/or created is a soft tissue, and wherein the matrix has:
an elasticity, expressed by a compression set, measured according to ASTM D395-16, equal to or lower than 10%, and
a compression elastic modulus (Ec) in the range 0.2 kPa to 100 kPa, whereby it has the capability to recover its original shape after a deformation up to 70% of compressive strain and 130% of tensile strain and is implantable by a surgical minimally invasive approach comprising injection into the implantation site or insertion by means of a needle or a tube.

5. The matrix according to claim 1, filled with and/or functionalized on the surface by:
radio-opaque substance(s) and/or object(s) for diagnosis of tumors and for relapse detection.

6. The matrix according to claim 1, chemically and/or physically functionalized and/or coated with cell receptor integrin binder(s) and/or cell adhesion molecules and macromolecules, wherein said integrin binder(s) and cell adhesion molecule(s) and macromolecule(s) are chosen from:
poly (L-lysine).

7. The matrix according to claim 1, including one or more additional constituents chosen from:
antitumor drugs, comprising anthracyclines and taxanes.

8. The matrix according to claim 1, arranged to release to the cultured cells and tissues, in vitro, and/or deliver to a local tissue near the implantation site and/or systemically via parenteral administration, in vivo, one or more of the following:
PPAR (Peroxisome Proliferator-Activated Receptor) gamma activator(s).

9. The matrix according to claim 1, consisting of a porous structure having pores/void spaces with heterogeneous shapes and sizes randomly distributed throughout the matrix volume.

10. The matrix according to claim 1, consisting of a plurality of units of predetermined shapes and sizes with interconnected open pores/void spaces, said units being formed of polymeric filaments defining the pores/void spaces and being repeated along the axes of a three-dimensional structure.

11. The matrix according to claim 1, further comprising three-dimensional channels interconnected with the pores/void spaces.

12. The matrix according to claim 1, wherein the void spaces/pores/repeating units are temporary filled with and sealed by a bioresorbable or bioeliminable or removable material, comprising a biomaterial different from the biomaterial of the matrix.

13. The matrix according to claim 1, for reconstruction, creation and/or regeneration of clinically relevant volumes of said soft and/or connective tissue and/or organs.

14. The matrix according to claim 13, for breast reconstruction and augmentation.

15. The matrix according to claim 1 for one or more of the following applications:
in first cell therapies, in which said matrix is seeded in vitro with cells and a living tissue is harvested and cultured in vitro through said matrix prior to implantation in the host organism;
in second cell therapies, in which said matrix is implanted without cells and a living tissue and/or cells is or are injected into said matrix already implanted in the host organism, immediately or at a later time;
as a bioreactor, where said matrix is implanted without cells and left to be colonized and vascularized by the host cells before injecting therapeutic cells into the colonized matrix;
cell delivery;
as a decellularized matrix, where said matrix is seeded in vitro with cells and a living tissue is harvested and cultured in vitro under static and/or dynamic condition to allow production of extracellular matrix within the pores/void spaces of said matrix, and the starting matrix plus cells plus extracellular matrix is then treated to eliminate the undesired cellular component;
in vitro biological assays, comprising drug screening tests, in which cells are seeded in vitro into said matrix and the cellular response to the tested drug is tested in vitro by means of the matrix plus said cells;
as coating for an implantable device, where said matrix is placed at the interface between said device and the surrounding/adjacent tissue to reduce the foreign body reaction against the device and minimise the capsular contracture; for release and/or delivery of bioactive molecules, peptides, drugs;
as implantable spacer for high precision radiation therapy;
as target for radiation therapy;
as implantable device for active follow-up after tumor resection and for the early diagnosis of tumors and detection of tumor relapse;
in wound healing and repair/reconstruction of lesioned portions of biological tissues and organs;
for aesthetic and/or cosmetic procedures comprising breast augmentation and/or congenital deformities treatment;
for cosmetic surgery.

16. A three-dimensional biodegradable implantable matrix with reduced foreign body response for reconstruction and/or regeneration and/or creation of soft and/or connective tissue and/or organs, the matrix having a solid component with interconnected pores/void spaces exhibiting a plurality of local thicknesses and a contact angle $\theta$ equal to or lower than 110°, the matrix being characterized by:
a density equal to or lower than 40 kg/m³;
said local thicknesses of the solid component falling in two distribution ranges, namely an upper local thickness range and a lower local thickness range, wherein the lower local thickness range is 2 µm to 15 µm and the upper local thickness range is 20 µm to 45 µm;
an average size of the pores/void spaces in the range 1,000 to 15,000 µm;

a surface roughness Ra of the solid component with an arithmetic mean equal to or lower than 3 µm.

17. The matrix according to claim 16, wherein
said density is in the range 5 kg/m$^3$ to 30 kg/m$^3$;
said average size of the pores/void spaces is in the range 2,000 µm to 15,000 µm, and has such a distribution that pores/void spaces with average size in the range 2,000 µm to 10,000 µm amount to 30% to 100% of the total pore/void space count;
said contact angle θ is in the range 10° to 90°.

18. The matrix according to claim 16, allowing an immediate matching between the mechanical properties of the volume filled with the matrix and the mechanical properties of the target tissue.

19. The matrix according to claim 16, wherein said tissue to be reconstructed and/or regenerated and/or created is a soft tissue, and wherein the matrix has:
an elasticity, expressed by a compression set, measured according to ASTM D395-16, equal to or lower than 10%, and
a compression elastic modulus (Ec) in the range 0.2 kPa to 100 kPa, whereby it has the capability to recover its original shape after a deformation up to 70% of compressive strain and 130% of tensile strain and is implantable by a surgical minimally invasive approach comprising injection into the implantation site or insertion by means of a needle or a tube.

* * * * *